United States Patent
Song et al.

(10) Patent No.: US 12,392,761 B1
(45) Date of Patent: Aug. 19, 2025

(54) EXPERIMENTAL APPARATUS AND METHOD FOR PLANAR INTERFACIAL SHEAR OF HYDRATE-BEARING SEDIMENT

(71) Applicant: Dalian University of Technology, Dalian (CN)

(72) Inventors: Yongchen Song, Dalian (CN); Yanghui Li, Dalian (CN); Peng Wu, Dalian (CN); Zhan Huang, Dalian (CN); Mingjun Yang, Dalian (CN); Lei Yang, Dalian (CN); Zheng Ling, Dalian (CN); Lunxiang Zhang, Dalian (CN); Bingbing Chen, Dalian (CN); Zhi Cui, Dalian (CN)

(73) Assignee: Dalian University of Technology, Dalian (CN)

( * ) Notice: Subject to any disclaimer, the term of this patent is extended or adjusted under 35 U.S.C. 154(b) by 0 days.

(21) Appl. No.: 19/194,161

(22) Filed: Apr. 30, 2025

(30) Foreign Application Priority Data

Jul. 9, 2024 (CN) ......................... 202410914111.7

(51) Int. Cl.
*G01N 33/24* (2006.01)
(52) U.S. Cl.
CPC .................... *G01N 33/24* (2013.01)
(58) Field of Classification Search
CPC .................................................. G01N 33/24
See application file for complete search history.

(56) References Cited

U.S. PATENT DOCUMENTS

| | | | | |
|---|---|---|---|---|
| 11,353,385 | B2* | 6/2022 | Hakimuddin | ............ G01N 3/12 |
| 2023/0033460 | A1* | 2/2023 | Kong | ........................ G01N 3/24 |

FOREIGN PATENT DOCUMENTS

| | | | | |
|---|---|---|---|---|
| CN | 111982782 | A | * 11/2020 | ........... G01N 23/046 |
| CN | 113622906 | A | 11/2021 | |
| CN | 114252351 | A | 3/2022 | |
| CN | 118191269 | A | 6/2024 | |

* cited by examiner

*Primary Examiner* — John Fitzgerald
(74) *Attorney, Agent, or Firm* — Bayramoglu Law Offices LLC

(57) ABSTRACT

An experimental apparatus for planar interfacial shear of a hydrate-bearing sediment includes a planar interfacial shear box, a torsional and axial loading device, a nitrogen gas source, a methane gas source, a pressure-volume controller, a water bath device, a back pressure valve, a gas-water separator, a gas flowmeter, and a data acquisition system. The planar interfacial shear box includes an upper pressing plate, an upper adapter, an upper thermal insulation plate, a ram adapter, a lower ram, an upper base, a lower base, a lower thermal insulation plate, a lower adapter, and a lower pressing plate that are coaxially connected in sequence from top to bottom. The experimental apparatus offers a simple specimen preparation method, enabling in-situ formation of a hydrate-bearing sediment in the shear box. The experimental apparatus ensures uniform stress distribution during shearing, and can acquire the interfacial shear mechanical characteristic between the hydrate-bearing sediment and a structure.

14 Claims, 2 Drawing Sheets

EXPERIMENTAL APPARATUS AND METHOD FOR PLANAR INTERFACIAL SHEAR OF HYDRATE-BEARING SEDIMENT

CROSS REFERENCE TO THE RELATED APPLICATIONS

This application is based upon and claims priority to Chinese Patent Application No. 202410914111.7, filed on Jul. 9, 2024, the entire contents of which are incorporated herein by reference.

TECHNICAL FIELD

The present disclosure belongs to the field of deep-sea oil and gas development research, and specifically relates to an experimental apparatus and method for planar interfacial shear of a hydrate-bearing sediment.

BACKGROUND

Natural gas hydrates, due to their high energy density, extensive distribution, and vast reserves, have emerged as a strategic high ground in the global energy landscape that nations worldwide are actively pursuing. Gas hydrates are widely distributed in the submarine strata of the South China Sea. During deep-sea oil and gas resource development, engineering disturbances such as pile foundation installation and drilling operations can trigger decomposition and reformation of shallow subsurface hydrates. This process will induce alterations in the interfacial mechanical characteristic between the hydrate-bearing sediment and structures, thereby compromising the bearing capacity of the pile foundation and diminishing stability of the offshore development platform. Therefore, investigating the interfacial mechanical characteristic between the hydrate-bearing sediment and structure holds critical significance for deep-sea oil and gas extraction.

Existing interfacial shear experimental apparatuses predominantly feature simple structures, failing to satisfy the low-temperature and high-pressure conditions requisite for hydrate formation. Moreover, these apparatuses can hardly measure pore pressure and temperature changes at the interface between the hydrate-bearing sediment and the structure, failing to describe the interaction mechanism at the interface. In 2021, China University of Petroleum (East China) proposed a testing apparatus and method (application No. 202110924314.0) for simulating a mechanical property of a marine energy soil-well interface during hydrate extraction. This apparatus modifies the upper and lower bases of a triaxial pressure chamber into L-shaped perforated steel blocks and perforated soft silicone. After being attached to each other, the semi-cylindrical soil specimen and the semi-cylindrical well interface are spliced with the base and fixed in the pressure chamber. The stress loading system applies an axial load, which is transmitted through the base to the soil specimen and the well interface, enabling shearing at the soil-well interface and enabling shear strength measurement. This method can stably form the soil specimen as the hydrate-bearing sediment to study the mechanical characteristic of the soil-well interface during hydrate extraction. However, the experimental apparatus has the following defects. 1. The stress distribution along the interface is uneven during experiments, potentially causing soil deformation during shearing. 2. The prepared semi-cylindrical soil specimen struggles to achieve tight contact with the well interface. 3. Temperature variations will affect performance of the soft silicone, compromising the accuracy of experimental data. 4. Limited by the thickness of the soft silicone, the shear displacement is insufficient for residual shear strength measurement.

In view of the above, the present disclosure develops a novel experimental apparatus for interfacial shear between a hydrate-bearing sediment and a structure based on existing interfacial shear experimental methods. The present disclosure can realistically simulate formation and decomposition of submarine hydrate-bearing sediments while controlling the stress state at the interface between the hydrate-bearing sediment and the structure, so as to provide theoretical guidance for further research on the bearing capacity and safety performance of the pile foundation.

SUMMARY

The present disclosure aims to overcome the defects in the prior art, and provides an experimental apparatus and method for planar interfacial shear of a hydrate-bearing sediment. The present disclosure can accurately measure a mechanical characteristic of the hydrate-bearing sediment under a large deformation, display data through a data acquisition system, and achieve simple operation with a reliable structure.

The present disclosure adopts the following technical solutions.

A first aspect of the present disclosure provides an experimental apparatus for planar interfacial shear of a hydrate-bearing sediment, including a planar interfacial shear box, a torsional and axial loading device, a nitrogen gas source, a methane gas source, a pressure-volume controller, a water bath device, a back pressure valve, a gas-water separator, a gas flowmeter, and a data acquisition system, where the planar interfacial shear box includes an upper pressing plate, an upper adapter, an upper thermal insulation plate, a ram adapter, a lower ram, an upper base, a lower base, a lower thermal insulation plate, a lower adapter and a lower pressing plate that are coaxially connected in sequence from top to bottom; a top of the lower ram is provided with a groove; a bottom of the groove is provided with a first serpentine channel; an opening at an upper part of the first serpentine channel is sealed by an upper ram; two ends of the first serpentine channel are connected to the water bath device through a temperature-controlled water inlet channel and a temperature-controlled water outlet channel, respectively; a top of the upper base is provided with a circular groove as a pressure cavity; the upper base is provided with a gas inlet channel communicated with the pressure cavity; the lower ram is provided with a gas outlet channel communicated with the pressure cavity; sealed vertical sliding and sealed circumferential rotation are performed between an inner wall of the circular groove and a bottom of the lower ram; a bottom of the circular groove is detachably connected to and covered by a permeable plate; the bottom of the lower ram is detachably connected to and covered by an upper test workpiece; a cylindrical specimen is placed between the permeable plate and the upper test workpiece; a temperature sensor is in contact with the specimen; a side of the permeable plate adjacent to the specimen is provided with a rib for torque transmission; a temperature control cylinder is circumferentially provided around the upper base; a bottom of the upper base below the specimen is provided with a second serpentine channel; and the temperature control cylinder and the second serpentine channel are connected to the water bath device;

the torsional and axial loading device includes an axial actuator located at an upper end and fixedly connected to a top of the upper pressing plate and a torsional actuator located at a lower end and fixedly connected to a bottom of the lower pressing plate; and the axial actuator, the planar interfacial shear box, and the torsional actuator are coaxially arranged; and the gas inlet channel is communicated with the nitrogen gas source and the methane gas source separately through a tubing having a second valve; the tubing is communicated with the pressure-volume controller through a branch having a first valve; the gas outlet channel is connected to a third valve, the back pressure valve, the gas-water separator and the gas flowmeter in sequence through a tubing; and the data acquisition system is connected to the pressure-volume controller, the water bath device, and the torsional and axial loading device.

Preferably, one end of the temperature-controlled water inlet channel and one end of the temperature-controlled water outlet channel are respectively connected to two sides of the first serpentine channel, and the other end of the temperature-controlled water inlet channel and the other end of the temperature-controlled water outlet channel pass through the upper ram and the ram adapter and are connected to the water bath device.

Preferably, the gas inlet channel includes one end located at the bottom of the circular groove and the other end located on a sidewall of the upper base; and the gas outlet channel includes one end located at the bottom of the lower ram and the other end located on a sidewall of the lower ram.

Preferably, the permeable plate and the upper base are detachably connected via a pin, and the upper test workpiece and the lower ram are detachably connected via a pin.

Preferably, the upper thermal insulation plate and the lower thermal insulation plate are made of polyether ether ketone (PEEK).

Preferably, the lower ram and the upper base are made of 316L stainless steel.

Preferably, a channel for mounting and fixing the temperature sensor passes through central-axis positions of the ram adapter, the upper ram, the lower ram and the upper test workpiece, and a probe end of the temperature sensor contacts the specimen.

Preferably, a guide ring and a Glyd ring are arranged in sequence from top to bottom at a connection between the upper base and lower ram to form a sealed sliding connection with a wall surface of the pressure cavity.

A second aspect of the present disclosure provides a testing method using the experimental apparatus for planar interfacial shear of a hydrate-bearing sediment according to any one of paragraphs in the first aspect, specifically including:

S1: controlling the torsional and axial loading device for axial displacement loading, such that the lower ram moves downward to enter the upper base, thereby sealing the pressure cavity; closing the first valve, the second valve, the third valve and the back pressure valve, and turning on the nitrogen gas source; opening the first valve, the second valve, and the third valve in sequence; applying leak detection liquid at a tubing connection to confirm no tubing leakage; and turning off the nitrogen gas source upon an inspection;

S2: subjecting the torsional and axial loading device to longitudinal motion wear calibration for axial loading and frictional resistance calibration for torsional loading, and determining a normal pressure loss Po during axial loading and a torsional loss torque Mo;

S3: uniformly mixing deionized water with a soil specimen according to target porosity and hydrate saturation; placing the mixed soil specimen into a specimen preparation mold, and compacting the mixed soil specimen layer by layer with a compaction tool; freezing a prepared cylindrical specimen at a sub-zero temperature for 24 h; and then taking out the prepared specimen;

S4: opening the back pressure valve, and evacuating a gas from the tubing; controlling the torsional and axial loading device for axial displacement loading, such that the lower ram moves upward and is opened; fixing the upper test workpiece to the bottom of the lower ram via a pin, and placing a filter paper between the upper test workpiece and the lower ram; fixing the permeable plate to the bottom of the circular groove in the upper base via a pin, and placing a filter paper between the permeable plate and the upper base; placing a filter paper and the prepared specimen in sequence on the permeable plate; and extending the lower ram into the circular groove, and compressing the specimen between the upper test workpiece and the permeable plate, ensuring that the pressure cavity remains sealed;

S5: opening the first valve and the second valve; opening and adjusting the back pressure valve to a maximum opening; turning on the methane gas source, and delivering methane gas into the pressure-volume controller and the pressure cavity separately through the tubing; turning off the methane gas source when a pressure of the pressure-volume controller rises to 0.5 MPa; adjusting the back pressure valve to a minimum opening, and closing the third valve; adjusting the pressure-volume controller to control a pore pressure until the pore pressure of the pressure-volume controller reaches 12 MPa; adjusting the pressure-volume controller to a constant-pressure mode; delivering the methane gas into the pressure cavity through the pressure-volume controller; adjusting a temperature in the pressure cavity through the water bath device to 15° C., thereby melting an ice in the specimen; determining that the specimen is fully gas-saturated when a methane gas volume in the pressure-volume controller ceases to decrease; and performing step S6 for in-situ hydrate formation;

S6: adjusting the temperature in the pressure cavity through the water bath device to 1° C., ensuring that a temperature of the specimen is lower than a hydrate phase equilibrium temperature; when the methane gas volume in the pressure-volume controller exhibits no further significant change, determining that water in a pore of the specimen has fully reacted with the methane gas to form a methane hydrate; and obtaining a consumption of the methane gas in the pressure-volume controller based on the methane gas volume stabilized in the pressure-volume controller in the step S5 and the methane gas volume stabilized in the pressure-volume controller in the step S6, and further calculating a saturation of the methane hydrate; and S7: determining a control mode of the pressure-volume controller based on an actual working condition; choosing stress control and strain control corresponding to different loading rates through the torsional and axial loading device to conduct a shear experiment on an interface between the specimen and the upper test workpiece, where the stress control is a control method that regulates a stress increment change rate, and the strain control is a control method that regulates a displacement change rate; acquiring and recording, by the data acquisition system, a torsional angle sensor reading, a stress sensor reading, a torque sensor reading, a displacement sensor reading, and a pore pressure sensor reading during the test; and analyzing a mechanical characteristic of a hydrate-structure interface based on acquired data and a calibration parameter obtained in the step S2.

Compared with the prior art, the present disclosure has the following beneficial effects:

(1) In the present disclosure, the upper test workpiece and the permeable plate can be replaced with different structures to conduct a dual-layer interfacial shear experiment and a fault sliding experiment, enhancing experimental diversity.

(2) The present disclosure innovatively eliminates the drawback that the existing planar interfacial shear experimental apparatus in soil mechanics cannot conduct an interfacial shear experiment on a hydrate-bearing sediment under low-temperature and high-pressure conditions.

(3) The testing method of the present disclosure features overall simplicity, convenient instrument operation, and high precision. It holds significant importance for studying interfacial shear mechanisms of hydrate-bearing sediments and provides data support for subsequent interfacial experimental simulations of hydrate-bearing sediments.

(4) In the present disclosure, S-shaped water bath grooves are provided in the groove at the top of the lower ram and at the bottom of the upper base. The temperature control cylinder is provided around the upper base. The thermal insulation plates are respectively provided between the upper adapter and the ram adapter and between the lower adapter and the lower base. In this way, the present disclosure achieves precise control of the experimental temperature in the planar interfacial shear box.

(5) The present disclosure achieves boundary condition control during interfacial shearing, enabling interfacial shear experiments under complex stress paths.

Figure 1:
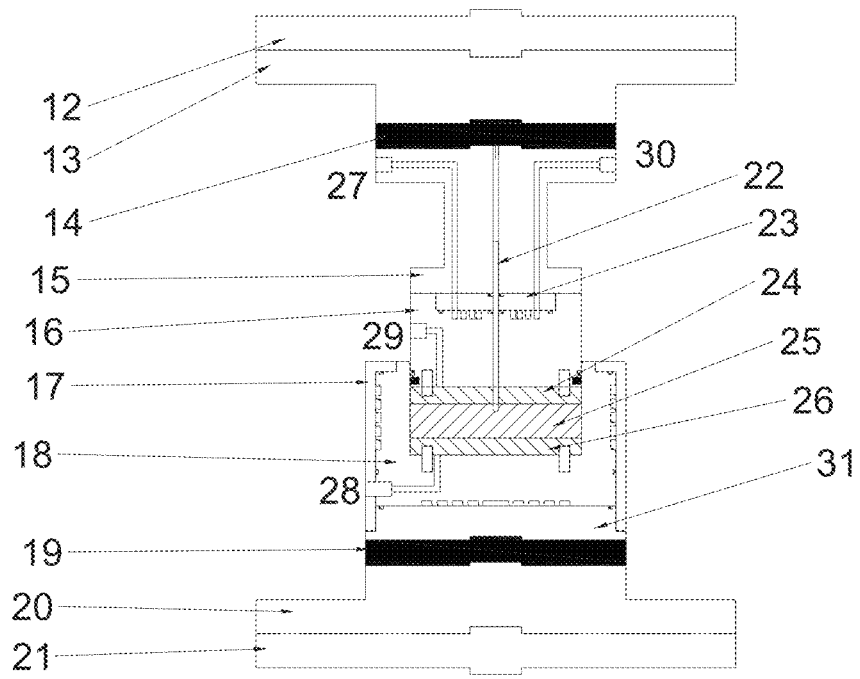
FIG. 1 is a structural diagram of a planar interfacial shear box of an experimental apparatus for planar interfacial shear of a hydrate-bearing sediment.

Reference Numerals: 1. planar interfacial shear box; 2. torsional and axial loading device; 3. nitrogen gas source; 4. methane gas source; 5. pressure-volume controller; 6. water bath device; 7. back pressure valve; 8. gas-water separator; 9. gas flowmeter; 10. data acquisition system; 11a. first valve; 11b. second valve; 11c. third valve; 12. upper pressing plate; 13. upper adapter; 14. upper thermal insulation plate; 15. ram adapter; 16. lower ram; 17. temperature control cylinder; 18. upper base; 19. lower thermal insulation plate; 20. lower adapter; 21. lower pressing plate; 22. temperature sensor; 23. upper ram; 24. upper test workpiece; 25. specimen; 26. permeable plate; 27. temperature-controlled water inlet channel; 28. gas inlet channel; 29. gas outlet channel; 30. temperature-controlled water outlet channel; and 31. lower base.

DETAILED DESCRIPTION OF THE EMBODIMENTS

The present disclosure is described in further detail below with reference to drawings and specific implementations. All the implementations of the present disclosure can be correspondingly combined on the premise that their technical features are not conflicted.

Figure 2:
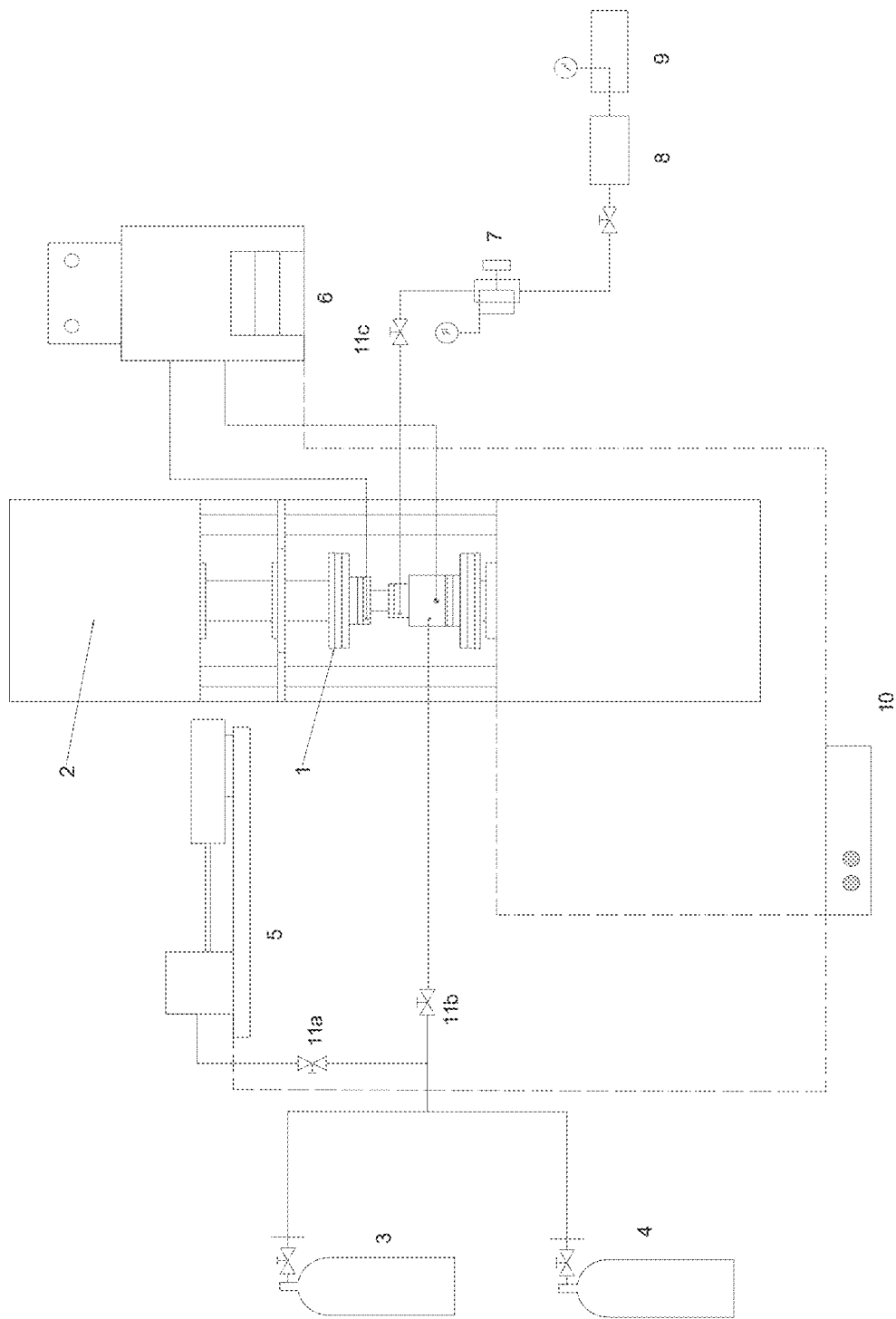
FIG. 2 is an overall systematic diagram of the experimental apparatus for planar interfacial shear of a hydrate-bearing sediment.

FIG. 2 shows an experimental apparatus for planar interfacial shear of a hydrate-bearing sediment provided by the present disclosure. The apparatus mainly includes planar interfacial shear box 1, torsional and axial loading device 2, nitrogen gas source 3, methane gas source 4, pressure-volume controller 5, water bath device 6, back pressure valve 7, gas-water separator 8, gas flowmeter 9, and data acquisition system 10.

The structure and connection of each component are specifically described below.

In the present disclosure, as shown in FIG. 1, the planar interfacial shear box 1 mainly includes lower pressing plate 21, lower adapter 20, lower thermal insulation plate 19, upper base 18, lower base 31, upper test workpiece 24, upper ram 23, lower ram 16, ram adapter 15, upper adapter 13, upper pressing plate 12, upper thermal insulation plate 14, temperature control cylinder 17, temperature sensor 22, specimen 25, and permeable plate 26. The upper pressing plate 12, the upper adapter 13, the upper thermal insulation plate 14, the ram adapter 15, the lower ram 16, the upper base 18, the lower base 31, the lower thermal insulation plate 19, the lower adapter 20, and the lower pressing plate 21 are coaxially connected in sequence from top to bottom.

It should be noted that in the present disclosure, unless otherwise specified, the "lower adapter 20", "ram adapter 15", and "upper adapter 13" refer to connecting component belonging to mechanical structures. The lower adapter 20 is configured to connect the lower thermal insulation plate 19 and the lower pressing plate 21. The upper adapter 13 is configured to connect the upper pressing plate 12 and the upper thermal insulation plate 14. The ram adapter 15 is configured to connect the upper thermal insulation plate 14 and the lower ram 16.

As a preferred embodiment of the present disclosure, the upper thermal insulation plate 14 and the lower thermal insulation plate 19 are made of a rigid material with excellent thermal insulation properties, such as polyether ether ketone (PEEK), which can prevent temperature loss from the pressure cavity through the upper adapter 13 and the lower adapter 20.

As a preferred embodiment of the present disclosure, the lower ram 16 and the upper base 18 are made of a corrosion-resistant and high-pressure-resistant alloy, such as 316L stainless steel, which can prevent an acidic substance from corroding the planar interfacial shear box 1.

In the present disclosure, as shown in FIG. 1, a top of the lower ram 16 is provided with a groove. A bottom of the groove is provided with a first serpentine channel. An opening at an upper part of the first serpentine channel is sealed by the upper ram 23 to prevent a water bath liquid in the first serpentine channel from leaking. Two ends of the first serpentine channel are connected to the water bath device 6 through temperature-controlled water inlet channel 27 and temperature-controlled water outlet channel 30, respectively.

As a preferred embodiment of the present disclosure, the temperature-controlled water inlet channel 27 includes one end communicated with one side of the first serpentine channel and the other end passing through the upper ram 23 and communicated with an outlet end of the water bath device 6. The temperature-controlled water outlet channel 30 includes one end communicated with the other side of the first serpentine channel and the other end passing through the ram adapter 15 and communicated with an inlet end of the water bath device 6.

In the present disclosure, as shown in FIG. 1, a top of the upper base 18 is provided with a circular groove as a pressure cavity. The upper base 18 is provided with gas inlet channel 28 communicated with the pressure cavity. The lower ram 16 is provided with gas outlet channel 29 communicated with the pressure cavity. In practical use, the gas inlet channel 28 may include one end located at a bottom of the circular groove and the other end located on a sidewall of the upper base 18. The gas outlet channel 29 may include one end located at a bottom of the lower ram 16 and the other end located on a sidewall of the lower ram 16. The bottom of the lower ram 16 can extend into the circular groove. An outer wall of the bottom of the lower ram 16 is slidable vertically along an inner wall of the circular groove in a sealed manner, and the upper base 18 is rotatable circumferentially around the lower ram 16 in a sealed manner. In practical use, a connection between the upper base 18 and lower ram 16 is sealed by a sealing ring. The bottom of the circular groove is detachably connected to the permeable plate 26. The bottom of the lower ram 16 is detachably connected to the upper test workpiece 24. The specimen 25 is cylindrical and placed between the permeable plate 26 and the upper test workpiece 24, and temperature sensor 22 is in contact with the specimen 25. A side of the permeable plate 26 adjacent to the specimen 25 is provided with a rib protrusion. The rib can be embedded into the specimen 25 to transmit a shear torque. A cross-section of the permeable plate 26 is identical to a cross-section of the bottom of the circular groove, such that the permeable plate 26 can completely cover the bottom of the circular groove. Similarly, a cross-section of the upper test workpiece 24 is identical to a cross-section of the bottom of the lower ram 16, such that the upper test workpiece 24 can completely cover the bottom of the lower ram 16.

As a preferred embodiment of the present disclosure, the permeable plate 26 and the upper base 18 are detachably connected via a pin. The upper test workpiece 24 and lower ram 16 are detachably connected via a pin. This connection method helps maintain stability of a test workpiece during a torsional shear experiment to prevent slippage, and allows removal of the test workpiece by vertical movement after the experiment. In the present disclosure, the upper test workpiece 24 and the permeable plate 26 can be replaced with different structures to conduct a dual-layer interfacial shear experiment and a fault sliding experiment.

As a preferred embodiment of the present disclosure, a channel for mounting and fixing the temperature sensor 22 passes through central-axis positions of the ram adapter 15, the upper ram 23, the lower ram 16 and the upper test workpiece 24, and a probe end of the temperature sensor 22 contacts the specimen 25. This structure reduces interferences caused by sliding between the temperature sensor 22 and the specimen 25 on the experimental structure during the torsional experiment.

In the present disclosure, as shown in FIG. 1, the temperature control cylinder 17 is circumferentially around the upper base 18. A bottom of the upper base 18 below the specimen 25 is provided with a second serpentine channel. The temperature control cylinder 17 and the second serpentine channel are connected to the water bath device 6, enhancing overall temperature stability control of the shear box.

In other words, in the planar interfacial shear box 1 of the present disclosure, a lower part of the upper pressing plate 12 is connected to a top of the upper adapter 13. A bottom of the upper adapter 13 is connected to a top of the upper thermal insulation plate 14. A bottom of the upper thermal insulation plate 14 is connected to a top of the ram adapter 15. A bottom of the upper ram 23 is fixed in the groove at the top of the lower ram 16. A bottom of the ram adapter 15 is connected to the top of the lower ram 16. The lower ram 16 is slidably provided in the pressure cavity of the upper base 18, and the upper base 18 and the lower ram 16 are sealed by with a sealing ring there-between. The temperature control cylinder 17 wraps around the upper base 18. The bottom of the lower ram 16 is fixedly connected to the upper test workpiece 24 via a pin. A bottom of the permeable plate 26 is connected to a bottom of the pressure cavity in the upper base 18. The cylindrical specimen 25 is placed between the upper test workpiece 24 and the permeable plate 26. The bottom of the upper base 18 is connected to a top of the lower base 31. A bottom of the lower base 31 is connected to a top of the lower thermal insulation plate 19. A bottom of the lower thermal insulation plate 19 is connected to a top of the lower adapter 20. A bottom of the lower adapter 20 is connected to a top of the lower pressing plate 21.

In the present disclosure, as shown in FIG. 2, the torsional and axial loading device 2 adopts a device structure from the prior art. It includes an axial actuator at an upper end, a torsional actuator at a lower end, as well as force and torque sensors (for recording stress sensor readings and torque sensor readings), displacement sensors, torsional angle sensors, etc. The specific structure is not redundantly described herein. The axial actuator at the upper end of the torsional and axial loading device 2 is fixedly connected to a top of the upper pressing plate 12. The torsional actuator at the lower end is fixedly connected to a bottom of the lower pressing plate 21. The axial actuator, the planar interfacial shear box 1, and the torsional actuator are coaxially arranged.

In the present disclosure, as shown in FIG. 2, the gas inlet channel 28 is communicated with the nitrogen gas source 3 and the methane gas source 4 separately through a tubing having second valve 11*b*. The tubing is communicated with the pressure-volume controller 5 through a branch having first valve 11*a*. The nitrogen gas source 3 and the methane gas source 4 each are provided with a valve for controlling opening and closing. The gas outlet channel 29 is connected to third valve 11*c*, the back pressure valve 7, the gas-water separator 8 and the gas flowmeter 9 in sequence through a tubing. The data acquisition system 10 is connected to the pressure-volume controller 5, the water bath device 6, and the torsional and axial loading device 2.

Based on the above experimental apparatus for planar interfacial shear of a hydrate-bearing sediment, the present disclosure further provides a testing method, including the following steps.

Before an experiment, it is confirmed whether all tubing in the apparatus are properly connected according to FIG. 2. Specifically:

A water bath channel on the temperature control cylinder 17 is connected to the water bath device 6 through flexible tubing (e.g., rubber hose) to achieve temperature control of the planar interfacial shear box 1. The gas inlet channel 28 is connected to the pressure-volume controller 5, the methane gas source 4, and the nitrogen gas source 3 through a pressure-resistant tubing (e.g., steel tubing) having the first valve 11*a* and the second valve 11*b* respectively to control a pore pressure in the sediment specimen. The methane gas source 4 supplies gas for in-situ hydrate formation in the sediment specimen, while the nitrogen gas source 3 primarily serves for tubing leak detection. The gas outlet channel 29 of the experimental apparatus for planar interfacial shear of a hydrate-bearing sediment is connected to the back pressure valve 7, the gas-water separator 8 and the gas flowmeter 9 through a pressure-resistant tubing having the third valve 11c to control a back pressure for the sediment specimen. The gas flowmeter 9 is configured to calculate a hydrate saturation change of the sediment specimen during a decomposition experiment. The temperature sensor 22, the pressure-volume controller 5, the torsional and axial loading device 2, and the water bath device 6 are connected to the data acquisition system 10 to achieve data acquisition of the apparatus in the present disclosure during the experiment.

After it is confirmed that all the tubing are properly connected, the following operations are performed sequentially.

S1: Experimental Leak Detection:

The torsional and axial loading device 2 is controlled for axial displacement loading, such that the lower ram 16 moves downward to enter the upper base 18, thereby sealing the pressure cavity. The first valve 11a, the second valve 11b, the third valve 11c and the back pressure valve 7 are closed, and the nitrogen gas source 3 is opened. Subsequently, the first valve 11a, the second valve 11b, and the third valve 11c are opened in sequence. Leak detection liquid is applied at a tubing connection to confirm no tubing leakage. If leakage occurs, a corresponding valve nut is retightened. An inspection is performed, and the nitrogen gas source 3 is turned off.

S2: Loss Calibration:

The torsional and axial loading device 21 is subjected to longitudinal motion wear calibration for axial loading and frictional resistance calibration for torsional loading, and normal pressure loss Po during axial loading and torsional loss torque Mo are determined.

S3: Specimen Preparation:

Deionized water is uniformly mixed with the soil specimen according to target porosity and hydrate saturation. The mixed soil specimen is placed into a specimen preparation mold and compacted layer by layer (e.g., 15 layers) with a compaction tool. The prepared cylindrical specimen 25 is frozen in a refrigerator at a sub-zero temperature for 24 h, and is then taken out.

S4: Specimen Mounting:

The back pressure valve 7 is opened, and a gas is evacuated from the tubing. The torsional and axial loading device 2 is controlled for axial displacement loading, such that the lower ram 16 moves upward and is opened. The upper test workpiece 24 is fixed to the bottom of the lower ram 16 via a pin, and a filter paper is placed between the upper test workpiece and the lower ram. The permeable plate 26 is fixed to the bottom of the circular groove in the upper base 18 via a pin, and a filter paper is placed between the permeable plate and the upper base. A filter paper and the prepared specimen 25 are placed in sequence on the permeable plate 26. The lower ram 16 is extended into the circular groove to compress the specimen 25 between the upper test workpiece 24 and the permeable plate 26, ensuring that the pressure cavity remains sealed.

S5: Specimen Saturation:

The first valve 11a and the second valve 11b are opened. The back pressure valve 7 is opened and adjusted to a maximum opening. The methane gas source 4 is turned on, and methane gas is delivered into the pressure-volume controller 5 and the pressure cavity separately through the tubing. When a pressure of the pressure-volume controller 5 rises to 0.5 MPa, the methane gas source 4 is turned off. The back pressure valve 7 is adjusted to a minimum opening, and the third valve 11c is closed. The pressure-volume controller 5 is adjusted to control a pore pressure until the pore pressure of the pressure-volume controller 5 reaches 12 MPa. The pressure-volume controller 5 is adjusted to a constant-pressure mode (stabilized at 12 MPa). The methane gas is delivered into the pressure cavity through the pressure-volume controller 5. A temperature in the pressure cavity is adjusted through the water bath device 6 to 15° C., thereby melting an ice in the specimen 25. When a methane gas volume in the pressure-volume controller 5 ceases to decrease, the specimen 25 is deemed fully gas-saturated. Step S6 is performed for in-situ hydrate formation.

S6: In-Situ Hydrate Formation:

The temperature in the pressure cavity is adjusted through the water bath device 6 to 1° C., ensuring that a temperature of the specimen 25 is lower than a hydrate phase equilibrium temperature. When the methane gas volume in the pressure-volume controller 5 exhibits no further significant change, water in a pore of the specimen 25 is deemed to have fully reacted with the methane gas to form a methane hydrate. Based on the methane gas volume stabilized in the pressure-volume controller 5 in the step S5 and the methane gas volume stabilized in the pressure-volume controller 5 in the step S6, a consumption of the methane gas in the pressure-volume controller 5 is obtained, and further a saturation of the methane hydrate is calculated.

S7: Specimen Shearing:

A control mode of the pressure-volume controller 5 is determined based on an actual working condition. Different control loading methods are chosen through the torsional and axial loading device 2 based on the actual working condition. That is, stress control and strain control are chosen to conduct a shear experiment on an interface between the specimen 25 and the upper test workpiece 24. Stress control is a control method that regulates a stress increment change rate, and strain control is a control method that regulates a displacement change rate. The two control methods can define different loading rates as required. The test can be manually stopped or automatically stopped based on a predefined failure criterion. During the test, a torsional angle sensor reading, a stress sensor reading, a torque sensor reading, a displacement sensor reading, and a pore pressure sensor reading are acquired and recorded via the data acquisition system 10. The mechanical characteristic of the hydrate under large-displacement shear is analyzed based on the acquired data and a calibration parameter obtained in the step S2.

The present disclosure aims to overcome deficiencies in the prior art (including Chinese Patent Application 202110924314.0: a testing apparatus and method for simulating a mechanical property of a marine energy soil-well interface during hydrate extraction). The present disclosure redesigns and optimizes the experimental apparatus for interfacial shear of a hydrate-bearing sediment, enabling in-situ formation of a hydrate-bearing sediment in the shear box and acquisition of the interfacial shear mechanical characteristic between the hydrate-bearing sediment and a structure. The present disclosure offers a simple specimen preparation method, achieves uniform stress distribution during shearing, and can obtain the residual interfacial shear strength. The present disclosure can offer more accurate and reliable experimental data, providing robust hardware support for investigating the interfacial mechanical characteristic between a hydrate-bearing sediment and a structure.

The above described are merely preferred embodiments of the present disclosure, and are not intended to limit the present disclosure. Various changes and transformations can be made by persons of ordinary skill in the relevant technical field without departing from the spirit and scope of the present disclosure. All technical solutions obtained by means of equivalent substitution or equivalent transformation should fall within the protection scope of the present disclosure.

The invention claimed is:

1. An experimental apparatus for planar interfacial shear of a hydrate-bearing sediment, comprising a planar interfacial shear box, a torsional and axial loading device, a nitrogen gas source, a methane gas source, a pressure-volume controller, a water bath device, a back pressure valve, a gas-water separator, a gas flowmeter, and a data acquisition system, wherein the planar interfacial shear box comprises an upper pressing plate, an upper adapter, an upper thermal insulation plate, a ram adapter, a lower ram, an upper base, a lower base, a lower thermal insulation plate, a lower adapter and a lower pressing plate, wherein the upper pressing plate, the upper adapter, the upper thermal insulation plate, the ram adapter, the lower ram, the upper base, the lower base, the lower thermal insulation plate, the lower adapter and the lower pressing plate are coaxially connected in sequence from top to bottom; a top of the lower ram is provided with a groove; a bottom of the groove is provided with a first serpentine channel; an opening at an upper part of the first serpentine channel is sealed by an upper ram; two ends of the first serpentine channel are connected to the water bath device through a temperature-controlled water inlet channel and a temperature-controlled water outlet channel, respectively; a top of the upper base is provided with a circular groove as a pressure cavity; the upper base is provided with a gas inlet channel communicated with the pressure cavity; the lower ram is provided with a gas outlet channel communicated with the pressure cavity; sealed vertical sliding and sealed circumferential rotation are performed between an inner wall of the circular groove and a bottom of the lower ram; a bottom of the circular groove is detachably connected to and covered by a permeable plate; the bottom of the lower ram is detachably connected to and covered by an upper test workpiece; a cylindrical specimen is placed between the permeable plate and the upper test workpiece; a temperature sensor is in contact with the cylindrical specimen; a side of the permeable plate adjacent to the cylindrical specimen is provided with a rib for torque transmission; a temperature control cylinder is circumferentially provided around the upper base; a bottom of the upper base below the cylindrical specimen is provided with a second serpentine channel; and the temperature control cylinder and the second serpentine channel are connected to the water bath device;

the torsional and axial loading device comprises an axial actuator located at an upper end and fixedly connected to a top of the upper pressing plate and a torsional actuator located at a lower end and fixedly connected to a bottom of the lower pressing plate; and the axial actuator, the planar interfacial shear box, and the torsional actuator are coaxially arranged; and the gas inlet channel is communicated with the nitrogen gas source and the methane gas source separately through a first tubing having a second valve; the first tubing is communicated with the pressure-volume controller through a branch having a first valve; the gas outlet channel is connected to a third valve, the back pressure valve, the gas-water separator and the gas flowmeter in sequence through a second tubing; and the data acquisition system is connected to the pressure-volume controller, the water bath device, and the torsional and axial loading device; and a channel for mounting and fixing the temperature sensor passes through central-axis positions of the ram adapter, the upper ram, the lower ram and the upper test workpiece, and a probe end of the temperature sensor contacts the cylindrical specimen.

2. The experimental apparatus for planar interfacial shear of the hydrate-bearing sediment according to claim 1, wherein a first end of the temperature-controlled water inlet channel and a first end of the temperature-controlled water outlet channel are respectively connected to two sides of the first serpentine channel, and a second end of the temperature-controlled water inlet channel and a second end of the temperature-controlled water outlet channel pass through the upper ram and the ram adapter and are connected to the water bath device.

3. The experimental apparatus for planar interfacial shear of the hydrate-bearing sediment according to claim 1, wherein the gas inlet channel comprises a first end located at the bottom of the circular groove and a second end located on a sidewall of the upper base; and the gas outlet channel comprises a first end located at the bottom of the lower ram and a second end located on a sidewall of the lower ram.

4. The experimental apparatus for planar interfacial shear of the hydrate-bearing sediment according to claim 1, wherein the permeable plate and the upper base are detachably connected via a first pin, and the upper test workpiece and the lower ram are detachably connected via a second pin.

5. The experimental apparatus for planar interfacial shear of the hydrate-bearing sediment according to claim 1, wherein the upper thermal insulation plate and the lower thermal insulation plate are made of polyether ether ketone (PEEK).

6. The experimental apparatus for planar interfacial shear of the hydrate-bearing sediment according to claim 1, wherein the lower ram and the upper base are made of 316L stainless steel.

7. The experimental apparatus for planar interfacial shear of the hydrate-bearing sediment according to claim 1, wherein a guide ring and a Glyd ring are arranged in sequence from top to bottom at a connection between the upper base and lower ram to form a sealed sliding connection with a wall surface of the pressure cavity.

8. A testing method using the experimental apparatus for planar interfacial shear of the hydrate-bearing sediment according to claim 1, comprising:

S1: controlling the torsional and axial loading device for axial displacement loading, such that the lower ram moves downward to enter the upper base, thereby sealing the pressure cavity; closing the first valve, the second valve, the third valve and the back pressure valve, and turning on the nitrogen gas source; opening the first valve, the second valve, and the third valve in sequence; applying leak detection liquid at a tubing connection to confirm no tubing leakage; and turning off the nitrogen gas source upon an inspection;

S2: subjecting the torsional and axial loading device to longitudinal motion wear calibration for axial loading and frictional resistance calibration for torsional loading, and determining a normal pressure loss $P_o$ during axial loading and a torsional loss torque $M_o$;

S3: uniformly mixing deionized water with a soil specimen according to target porosity and hydrate saturation to obtain a mixed soil specimen; placing the mixed soil specimen into a specimen preparation mold, and compacting the mixed soil specimen layer by layer with a compaction tool to obtain a prepared cylindrical specimen; freezing the prepared cylindrical specimen at a sub-zero temperature for 24 h; and then taking out the prepared cylindrical specimen;

S4: opening the back pressure valve, and evacuating a gas from the second tubing; controlling the torsional and axial loading device for axial displacement loading, such that the lower ram moves upward and is opened; fixing the upper test workpiece to the bottom of the lower ram via a second pin, and placing a first filter paper between the upper test workpiece and the lower ram; fixing the permeable plate to the bottom of the circular groove in the upper base via a first pin, and placing a second filter paper between the permeable plate and the upper base; placing a third filter paper and the prepared cylindrical specimen in sequence on the permeable plate; and extending the lower ram into the circular groove, and compressing the prepared cylindrical specimen between the upper test workpiece and the permeable plate, ensuring that the pressure cavity remains sealed;

S5: opening the first valve and the second valve; opening and adjusting the back pressure valve to a maximum opening; turning on the methane gas source, and delivering methane gas into the pressure-volume controller and the pressure cavity separately through the first tubing; turning off the methane gas source when a pressure of the pressure-volume controller rises to 0.5 MPa; adjusting the back pressure valve to a minimum opening, and closing the third valve; adjusting the pressure-volume controller to control a pore pressure until the pore pressure of the pressure-volume controller reaches 12 MPa; adjusting the pressure-volume controller to a constant-pressure mode; delivering the methane gas into the pressure cavity through the pressure-volume controller; adjusting a temperature in the pressure cavity through the water bath device to 15° C., thereby melting an ice in the prepared cylindrical specimen; determining that the prepared cylindrical specimen is fully gas-saturated when a methane gas volume in the pressure-volume controller ceases to decrease; and performing step S6 for in-situ hydrate formation;

S6: adjusting the temperature in the pressure cavity through the water bath device to 1° C., ensuring that a temperature of the prepared cylindrical specimen is lower than a hydrate phase equilibrium temperature; when the methane gas volume in the pressure-volume controller exhibits no further significant change, determining that water in a pore of the prepared cylindrical specimen has fully reacted with the methane gas to form a methane hydrate; and obtaining a consumption of the methane gas in the pressure-volume controller based on the methane gas volume stabilized in the pressure-volume controller in the step S5 and the methane gas volume stabilized in the pressure-volume controller in the step S6, and further calculating a saturation of the methane hydrate; and S7: determining a control mode of the pressure-volume controller based on an actual working condition; choosing stress control and strain control corresponding to different loading rates through the torsional and axial loading device to conduct a shear experiment on an interface between the prepared cylindrical specimen and the upper test workpiece, wherein the stress control is a control method that regulates a stress increment change rate, and the strain control is a control method that regulates a displacement change rate; acquiring and recording, by the data acquisition system, a torsional angle sensor reading, a stress sensor reading, a torque sensor reading, a displacement sensor reading, and a pore pressure sensor reading during the test; and analyzing a mechanical characteristic of a hydrate-structure interface based on acquired data and a calibration parameter obtained in the step S2.

9. The testing method according to claim 8, wherein in the experimental apparatus for planar interfacial shear of the hydrate-bearing sediment, a first end of the temperature-controlled water inlet channel and a first end of the temperature-controlled water outlet channel are respectively connected to two sides of the first serpentine channel, and a second end of the temperature-controlled water inlet channel and a second end of the temperature-controlled water outlet channel pass through the upper ram and the ram adapter and are connected to the water bath device.

10. The testing method according to claim 8, wherein in the experimental apparatus for planar interfacial shear of the hydrate-bearing sediment, the gas inlet channel comprises a first end located at the bottom of the circular groove and a second end located on a sidewall of the upper base; and the gas outlet channel comprises a first end located at the bottom of the lower ram and a second end located on a sidewall of the lower ram.

11. The testing method according to claim 8, wherein in the experimental apparatus for planar interfacial shear of the hydrate-bearing sediment, the permeable plate and the upper base are detachably connected via the first pin, and the upper test workpiece and the lower ram are detachably connected via the second pin.

12. The testing method according to claim 8, wherein in the experimental apparatus for planar interfacial shear of the hydrate-bearing sediment, the upper thermal insulation plate and the lower thermal insulation plate are made of polyether ether ketone (PEEK).

13. The testing method according to claim 8, wherein in the experimental apparatus for planar interfacial shear of the hydrate-bearing sediment, the lower ram and the upper base are made of 316L stainless steel.

14. The testing method according to claim 8, wherein in the experimental apparatus for planar interfacial shear of the hydrate-bearing sediment, a guide ring and a Glyd ring are arranged in sequence from top to bottom at a connection between the upper base and lower ram to form a sealed sliding connection with a wall surface of the pressure cavity.

* * * * *